United States Patent [19]

Pfrengle

[11] Patent Number: 5,849,802
[45] Date of Patent: Dec. 15, 1998

[54] FUNGICIDAL SPIROCYCLIC AMINES

[75] Inventor: Waldemar Franz Augustin Pfrengle, Seibersbach, Germany

[73] Assignee: American Cyanamid Company, Madison, N.J.

[21] Appl. No.: 722,787

[22] Filed: Sep. 27, 1996

[51] Int. Cl.[6] .................. A61K 31/13; A61K 31/535; A61K 31/445; C07C 211/00

[52] U.S. Cl. .............. 514/660; 514/659; 514/231.2; 514/317; 564/457; 564/455; 564/454; 564/453; 544/106; 546/192

[58] Field of Search .................. 564/457, 453, 564/454, 455; 514/660, 659, 231.2, 317; 544/106; 546/192; 568/367, 303, 445, 420

[56] References Cited

U.S. PATENT DOCUMENTS

| | | | |
|---|---|---|---|
| 3,214,470 | 10/1965 | Grogan | 564/457 |
| 3,686,399 | 8/1972 | Sanne et al. | 424/248 |
| 4,005,224 | 1/1977 | Tankersley, Jr. | 424/325 |
| 4,202,894 | 5/1980 | Pfiffner | 424/248.4 |
| 4,261,866 | 4/1981 | Barton et al. | 568/367 |
| 4,639,330 | 1/1987 | Sprecker et al. | 568/367 |
| 4,800,202 | 1/1989 | Weissmuller et al. | 514/227 |
| 4,804,659 | 2/1989 | Weissmuller et al. | 514/237.8 |
| 4,851,405 | 7/1989 | Krame et al. | 514/212 |
| 5,032,616 | 7/1991 | Sauter et al. | 514/579 |
| 5,071,851 | 12/1991 | Buschmann et al. | 514/238.8 |
| 5,175,295 | 12/1992 | Zipplies et al. | 546/15 |
| 5,268,351 | 12/1993 | Zipplies et al. | 504/130 |
| 5,462,944 | 10/1995 | Pfrengle | 514/275 |
| 5,489,599 | 2/1996 | Carter et al. | 514/317 |

FOREIGN PATENT DOCUMENTS

| | | |
|---|---|---|
| 0 635 503 A1 | 7/1994 | Germany . |
| 0 349 247 B1 | 6/1989 | United Kingdom . |

OTHER PUBLICATIONS

March, Jerry, *Reactions, Mechanisms, and Structure,* Advanced Organic Chemistry, Third Edition, 1985, pp. 798–801.

*Primary Examiner*—Deborah C. Lambkin
*Attorney, Agent, or Firm*—Timothy J. Babcock

[57] ABSTRACT

New antimicrobial spirocarbocyclic compounds are described, having the general formula I,

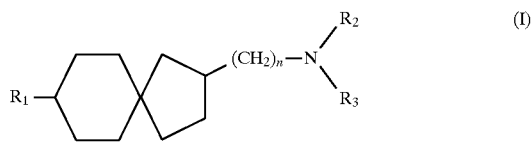

or an acid-addition salt thereof, in which $R_1$ represents an optionally substituted alkyl, cycloalkyl, cycloalkylalkyl, alkoxy, cycloalkoxy, alkoxyalkyl, aralkyl group $R_2$ and $R_3$ each independently represent hydrogen or an optionally substituted alkyl, alkenyl, alkynyl, cycloalkyl, cycloalkylalkyl, bicycloalkyl, tricycloalkyl, alkoxyalkyl, aralkyl, aryl or haloaralkyl, a 4- to 6-membered heterocyclyl, tetrahydrofuryl or dioxolanyl group, or $R_2$ and $R_3$, together represents an optionally substituted, saturated or unsaturated chain which may optionally contain one or more oxygen atoms and which may optionally be aryl- or cycloalkyl-fused, and n represents zero or an integer from 1 to 3. The invention further relates to the preparation of the above spirocarbocyclic compounds, intermediates prepared during the synthesis of these compounds, compositions containing the compounds and their use as fungicides in the control of phytopathogenic fungi.

16 Claims, No Drawings

FUNGICIDAL SPIROCYCLIC AMINES

BACKGROUND OF THE INVENTION

The present invention relates to certain new spiocarbocyclic compounds having fungicidal properties, processes for the preparation of these compounds, novel intermediates used in said process, fungicidal compositions containing the compounds and the use of the compounds as fungicides for the control of phytopathogenic fungi.

In U.S. Pat. Nos. 4,851,405, 5,175,295, 5,268,351, EP 349247 and EP 635503 fungicidal spiroheterocyclic compounds have been described. These known compounds contain a substituted cyclohexyl ring in spiro conjunction with a substituted heterocyclic five or six membered ring. The substituents of the cyclohexyl ring are usually (substituted) (branched) alkyl or phenyl groups. The substituents of the heterocyclic ring are usually (substituted) (cyclo)alkyl- or dialkyl-amino-methyl or dialkyl-amino-polymethyl groups, including alkylene-amino-methyl or alkylene-amino-polymethyl groups.

SUMMARY OF THE INVENTION

It has now been found that certain new Spirocarbocyclic compounds show excellent fungicidal activity against certain phytopathogenic fungi, for instance against *Plasmopora viticola, Botrytis cinerea, Erysiphe graminis, Pseudocercosporella herpotrichoides, Rhizoctonia solani, Venturia inaegualis* and *Alternaria solani*.

The present invention therefore relates to compounds of the formula I

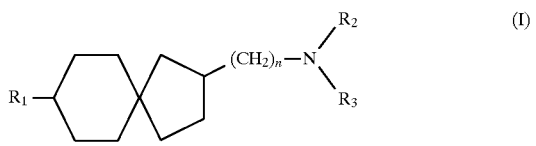

or an acid-addition salt thereof, in which $R_1$ represents an optionally substituted alkyl, cycloalkyl, cycloalkylalkyl, alkoxy, cycloalkoxy, alkoxyalkyl, aralkyl or aryl group;

$R_2$ and $R_3$ each independently represent hydrogen or an optionally substituted alkyl, alkenyl, alkynyl, cycloalkyl, cycloalkylalkyl, bicycloalkyl, tricycloalkyl, alkoxyalkyl, aralkyl, aryl or haloaralkyl, a 4- to 6-membered heterocyclyl, tetrahydrofuryl or dioxolanyl group, or $R_2$ and $R_3$, together represents an optionally substituted, saturated or unsaturated chain which may optionally contain one or more oxygen, nitrogen or sulphur atoms and which may optionally be aryl- or cycloalkyl-fused, and n represents zero or an integer from 1 to 3.

DETAILED DESCRIPTION OF THE INVENTION

The invention especially relates to compounds of the general formula I in which any alkyl part of any of the groups $R_1$ to $R_3$, which may be straight chained or branched, contains up to 12 carbon atoms, preferably up to 10 carbon atoms, more preferably up to 9 carbon atoms, any alkenyl or alkynyl part of any of the substituents $R_1$ to $R_3$ contains up to 12 carbon atoms, preferably up to 10 carbon atoms, more preferably up to 9 carbon atoms, any cycloalkyl part of any of the substituents $R_1$ to $R_3$ contains from 3 to 10 carbon atoms, preferably from 3 to 8 carbon atoms, more preferably from 3 to 6 carbon atoms, any saturated or unsaturated chain, especially carbon chain, contains from 3 to 10 chain members, preferably from 4 to 6 carbon atoms, and any aryl part of any of the substituents $R_1$ to $R_3$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably C3-6 cycloalkyl, cycloalkenyl, preferably $C_{3-6}$ cycloalkenyl, haloalkyl, preferably $C_{1-6}$ haloalkyl, halocycloalkyl, preferably C3-6 halocycloalkyl, alkoxy, preferably $C_{1-6}$ alkoxy, haloalkoxy, preferably $C_{1-6}$ haloalkoxy, phenyl, halo- or dihalo-phenyl or pyridyl groups. Any alkyl, alkenyl or alkynyl group may be linear or branched. A 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitably denotes a fluorine, chlorine or bromine atom.

The invention especially relates to compounds of the general formula I in which $R_1$ represents a $C_{1-10}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group.

Preferably $R_1$ represents a $C_{1-8}$, suitably $C_{1-6}$, alkyl group, especially a branched alkyl group, more especially secondary and tertiary alkyl groups as secondary butyl, tertiary butyl and tertiary amyl groups. More preferably, $R_1$ represents a t-butyl or t-amyl group.

The invention further especially relates to compounds of the general formula I in which $R_2$ and $R_3$ each independently represent a hydrogen atom, a $C_{1-12}$ alkyl, especially $C_{3-10}$ alkyl, $C_{2-6}$ alkenyl, $C_{2-6}$ alkynyl, $C_{3-8}$ cycloalkyl-$C_{1-6}$ alkyl, $C_{3-8}$ cycloalkyl, phenyl, phenyl-$C_{1-6}$ alkyl, especially benzyl, halophenyl-$C_{1-6}$ alkyl or pyridyl-$C_{1-6}$ alkyl group, or $R_2$ and $R_3$ together represent a saturated carbon chain containing three to eight carbon atoms while optionally one or more additional oxygen atoms may be present in the chain and which chain may optionally be aryl- or cycloalkyl-fused. Preferably $R_2$ and $R_3$ each independently represent a hydrogen atom, a $C_{2-12}$ alkyl, $C_{2-5}$ alkenyl, $C_{5-7}$ cyclo-$C_{1-2}$ alkyl, $C_{5-7}$ cycloalkyl or phenyl-$C_{1-2}$ alkyl group, or $R_2$ and $R_3$ together represent a saturated chain containing four or five carbon atoms while optionally additional oxygen atoms may be present and which chain optionally may be aryl- or cycloalkyl-fused, especially cyclopentyl, cyclohexyl or cycloheptyl fused, each of the above groups optionally substituted by one or more halogen atoms, especially chlorine and/or fluorine atoms, or $C_{1-4}$ alkyl, $C_{1-4}$ haloalkyl, $C_{4-6}$ cycloalkenyl or $C_{1-4}$ alkoxy groups.

The invention also especially relates to compounds of the general formula I in which $R_2$ represents a hydrogen atom or a methyl group, preferably a hydrogen atom.

The invention especially relates to compounds of the general formula I in which n represents 0, 1 or 2, particularly 0.

A particular preferred sub-group of compounds of the general formula I is that in which $R_1$ represents a butyl, pentyl or phenyl group, especially a t-butyl or t-amyl group. Another particular sub-group is that in which $R_2$ and $R_3$ each independently represent a hydrogen atom or a linear or branched $C_{1-12}$ alkyl group, especially a $C_{1-10}$ alkyl group, an allyl, $C_{3-7}$ cycloalkyl optionally fused with a cyclohexyl group, benzyl or phenyl group, or $R_2$ and $R_3$ together represent a saturated $C_{4-7}$ carbon chain, especially a $C_{4-6}$ carbon chain, which optionally may contain an additional oxygen atom and which optionally may be fused with a cyclohexyl ring, each of the above groups optionally substituted by a fluorine, chlorine or bromine atom or one or two methyl groups, a t-butyl, cyclohexyl, cyclohexenyl, phenyl or pyridyl group.

The present invention further provides a process for the preparation of compounds of the general formula I as defined hereinbefore or acid-addition salts thereof, which process comprises reaction of a compound of the general formulae IIa or IIb wherein n is 0, 1 or 2 and $R_1$ is defined hereinbefore, with a compound of the general formula III

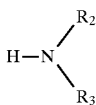

III in which $R_2$ and $R_3$ are as defined hereinbefore, under reducing conditions.

Suitable reducing conditions for the reductive amination are well known in the literature. See for instance J. March, Advanced Organic Chemistry, J. Wiley & Sons, New York, 1985. Suitable reducing agents are formic acid (Leuckart-Wallach reduction), complex metal hydrides such as cyanoborohydride or hydrogen gas together with a hydrogenation catalyst, e.g. Raney nickel.

The starting compounds of formulae IIa and IIb are novel. Therefore, the invention relates also to the novel starting compounds of formulae IIa and IIb.

The compounds of formula IIa can be prepared according to reaction scheme 1, in which the following expressions have been used:

STEP 1: "strong base" represents a metal organic compound, preferably a metal dialkylamide or an alkali metal alkane, in particular lithium diisopropylamide; "allylhalide" represents allylchloride, allylbromide or allyliodide.

STEP 2: "peroxoacid" represents suitably an organic peroxoacid, preferably an optionally substituted perbenzoic acid, in particular m-chloroperbenzoic acid.

STEP 3: "reduction" represents a reduction process carried out with a complex metal hydride, preferably a complex aluminum hydride or borohydride, in particular lithium aluminum hydride.

STEP 4: "oxidation" represents a oxidation process carried out in the presence of agents being capable of oxidizing primary alcohols to aldehydes, in particular with dimethyl sulfoxide in the presence of oxalyl chloride and a base.

STEP 5: "aldol condensation" represents a condensation process, preferably carried out in the presence of a base such as a metal dialkylamide or a metal hydroxide or a metal alkoxide.

STEP 6: "hydrogenation" represents a hydrogenation process carried out in the presence of a heterogeneous catalyst, in particular in the presence of Raney nickel and/or palladium.

Scheme 1

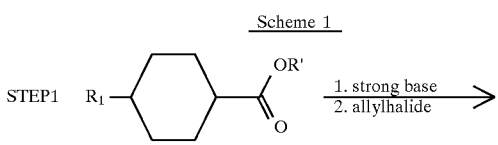

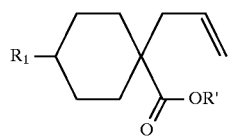

-continued
Scheme 1

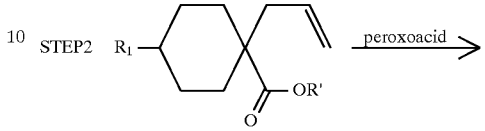

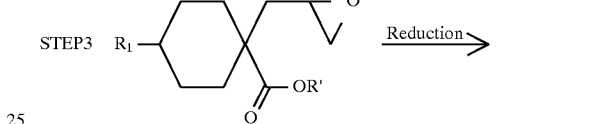

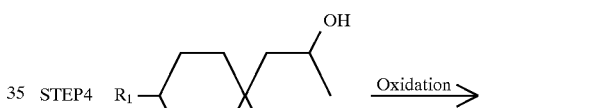

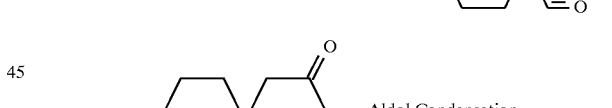

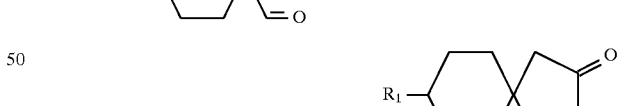

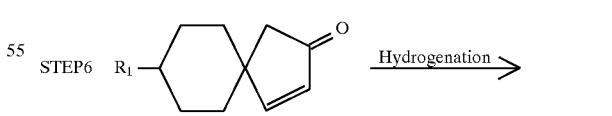

wherein R represents a $C_{1-10}$ alkyl, $C_{3-6}$ cycloalkyl, $C_{3-8}$ cycloalkyl-$C_{1-6}$ alkyl, $C_{1-10}$ alkoxy-$C_{1-6}$ alkyl, phenyl or benzyl group.

The compounds of formula IIb can be obtained from formula IIa according to reaction scheme 2, in which the following expressions have been used:

"hydrogenation": as described for STEP 6 of scheme 1;
"reduction": as described for STEP 3 of scheme 1;
"oxidation": as described for STEP 4 of scheme 1;

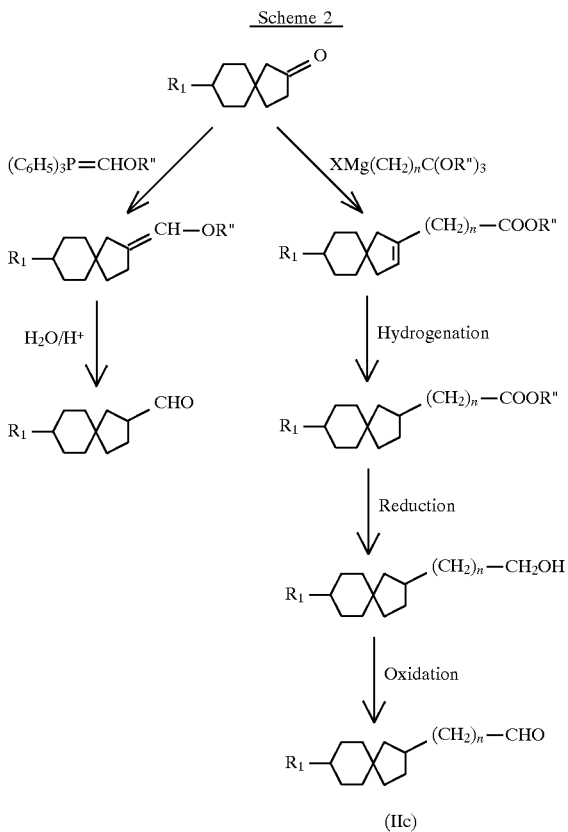

wherein n is 1 or 2;
R" represents a $C_{1-10}$ alkyl, $C_{3-6}$ cycloalkyl, $C_{3-8}$ cycloalkyl-$C_{1-6}$ alkyl, $C_{1-10}$ alkoxy-$C_{1-6}$ alkyl or phenyl group; X denotes halogen, preferably Cl, Br or I. The compounds (IIc) wherein n is 2 may be further reacted to convert the aldehyde moiety to an imino group followed by reduction to form the compounds of Formula I wherein n is 3.

Starting compounds of the general formula III are well known in the literature, and many of them are commercially available.

The reductive amination process of the present invention is suitably carried out in the presence of an organic solvent, for example an ether, an alcohol or a carboxylic acid such as acetic acid.

The process is suitably carried out at a temperature in the range of 0° to 150° C., especially between 40° and 120° C., in the case of formic acid as reducing agent or at temperatures between 0° and 50° C. in the case of complex borohydrides as reducing agents.

In an alternative process for the preparation of the compounds of the present invention the starting compound of formula IIa is first converted into the corresponding aminospiro(4,5)decane compound, for instance by reaction with hydroxylamine followed by reduction of the obtained oxime. The 3-amino compound is thereafter alkylated, especially with a ketone or aldehyde under suitable reducing conditions or with an alkylating agent. The reaction of the ketone starting material and hydroxylamine is well known in the literature. The reaction may be carried out in an organic solvent/water mixture at temperature between 20° and 100° C. The reduction of the oxime compounds is also well known in the literature. The reduction can be carried out with complex metal hydrides, for instance lithium aluminium hydride, in an organic solvent, e.g. tetrahydrofuran, at temperatures between 40° and 80° C. The alkylation of amines using ketones or aldehydes is well known in the literature, and is described hereinbefore. The alkylation using alkylating agents is also well known in the literature. Alkylating agents, for instance (substituted) alkyl halides may be used in suitable, inert organic solvents at temperatures between 40° and 100° C.

The present invention also provides a process for the preparation of compounds of the general formula I as defined hereinbefore, or acid addition salts thereof, and in which n is 1, which process comprises reduction of a compound of the general formula IIa as defined hereinbefore to an alcohol, activation of the alcohol, followed by reaction with hydrogen cyanide, a salt thereof or with trialkylsilyl cyanide in the presence of a Lewis acid, followed by reduction of the obtained cyanide group and alkylation of the amine obtained, especially with a ketone or aldehyde under suitable reducing conditions or an alkylating reagent. The reduction of the carbonyl group of the starting compound of formula IIa can be carried out according to methods well known in the literature, for example by reduction with a complex metal hydride such as sodium borohydride. The activation of the alcohol can also be carried out according to methods well known in the literature, for instance by reaction with alkyl- or arylsulfonylchloride. The substition of the activated hydroxy group is suitably carried out in a polar organic solvent, for instance an alcohol, an ether or a ketone using hydrogen cyanide or a salt thereof. The substitution with a trialkylsilyl cyanide, as for example with trimethylsilyl cyanide, is carried out in an aprotic solvent, for instance in an ether or a halogenalkane, such as dichloromethane, in the presence of a Lewis acid. The reduction of the cyano group is also well known in the literature, and can be performed as described hereinbefore. The alkylation of the 3-aminomethyl group may be carried out as described hereinbefore.

The present invention also provides a process for the preparation of a compound of the general formula I as defined hereinbefore, or acid addition salts thereof, and in which n represents 2, which process comprises reaction of a compound of the general formula IIa as defined hereinbefore, with cyanoacetic acid (Knoevenagel-Doebner reaction) followed by reduction of the compound obtained into an amine, and alkylation of the amine, especially with a ketone or aldehyde under suitable reducing conditions or an alkylating agent. The reaction of the ketone starting material and cyanoacetic acid is suitably carried out in a polar organic solvent such as pyridine. The reduction of the cyano group and the alkylation of the 3-aminoethyl group may be carried out as described hereinbefore.

Suitably all reactions are carried out using substantially equimolar amounts of the reactants. However, it can be expedient to use one reactant in excess.

It will be appreciated that in addition to the above described reaction steps additional chemical modifications can be made to the compounds and intermediates, e.g. introduction or amendment of certain substituents, additional alkylation reactions etc.

The invention also provides fungicidal compositions comprising at least one of the compounds according to general formula I or an acid addition salt thereof, as well as methods of combating fungi at a locus comprising treatment of the locus with a compound of formula I or an acid addition salt thereof as defined hereinbefore, or with a composition as defined in this specification. The locus to be treated especially comprises plants subject to or subjected to fungal attack, seeds of such plants or the medium in which the plants are growing or are to be grown.

The fungicidal composition comprises a carrier and, as active ingredient, a compound of the general formula I or an acid addition salt thereof.

A method of making such a composition is also provided, which comprises bringing a compound of the general formula I as defined above or an acid addition salt thereof into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

The invention further relates to the use as a fungicide of a compound of formula I as defined hereinbefore or a composition as defined hereinbefore.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a plant, or could include an adhesive component enabling them to be applied directly to the stem of a vine plant.

The present invention still further provides the use as a fungicide of a compound of the general formula I as defined above or a composition as defined above.

The present invention is of wide applicability in the protection of crop plants against fungal attack. Typical crops which may be protected include cereals, especially wheat and barley, rice, vines, vegetales, especially sugarbeet, potatoes, tomatoes, top fruit, especially apples, and cucumber. The duration of protection is normally dependent on the individual compound selected, and also a variety of external factors, such as climate, whose impact is normally mitigated by the use of a suitable formulation. The compounds of the present invention are especially suitable to combat Erysiphe graminis in cereals.

The invention is further illustrated by the following examples.

EXAMPLES 1–180

2-Amino-spiro(4,5)decane Derivatives (i) Preparation of ethyl 1-allyl-4-t-butylcyclohexylcarboxylate

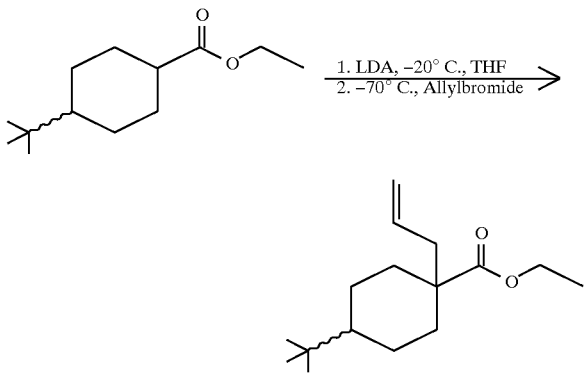

To a cold (−20° C.) solution of lithium diisopropylamide (0.2 mol) in tetrahydrofuran (300 ml) is added ethyl 4-t-butylcyclohexylcarboxylate (42.5 g, 0.2 mol) in tetrahydrofuran (100 ml). The reaction mixture is stirred for 1h at −20° C. and is then cooled to −70° C. Allylbromide (24.5 g, 0.2 mol) is added and the reaction mixture is allowed to warm up to room temperature over night. The reaction mixture is then quenched with saturated aqueous ammonium chloride solution (200 ml) and most of the organic solvent is distilled off under reduced pressure. From the remainder the product is extracted with toluene (500 ml). The organic layer is separated, dried with magnesium sulphate and concentrated in vacuo to yield an oil (51 g). Distillation in vacuo (b.p. 75°–82° C./ 0.03 mbar) furnishes the pure product as a colourless oil (46 g).

(ii) Preparation of ethyl 1-(2,3-epoxyprop-1-yl)-4-t-butylcyclohexylcarboxylate

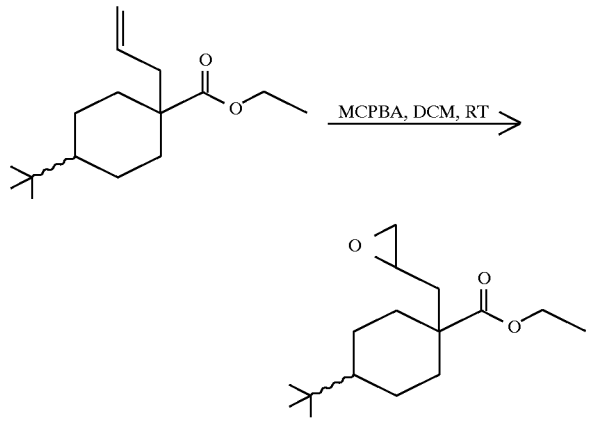

To a solution of 3-chloroperbenzoic acid (25 g, 0.080 mol) in dichloromethane (200 ml) is added ethyl 1-allyl-4-t-butylcyclohexylcarboxylate (17 g, 0.067 mol) in dichloromethane (200 ml). The reaction mixture is stirred at room temperature over night. Precipitated 3-chlorobenzoic acid is filtered off and the filtrate is washed twice with saturated aqueous sodium bicarbonate and 5% aqueous sodium bisulfite. Drying and evaporation of the solvent yields the product as a colourless oil (17 g).

(iii) Preparation of 1-hydroxymethyl-1-(2-hydroxyprop-1-yl)-4-t-butylcyclohexane

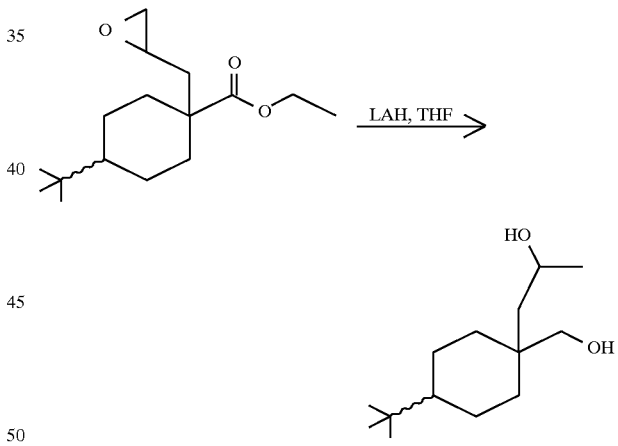

To lithium aluminumhydride (5.0 g, 0.132 mol) in tetrahydrofuran (100 ml) is added 1-(2,3-epoxyprop-1-yl)-4-t-butylcyclohexylcarboxylate (17 g, 0.063 mol) as a solution in tetrahydrofuran (100 ml) at room temperature. The mixture is stirred over night and excess LAH is hydrolysed by careful addition of saturated aqueous sodium sulfate. Precipitated inorganics are filtered and the filtrate is dried with magnesium sulfate. Evaporation of the solvent furnishes 14 g of crude product which is recrystalized from light petroleum to yield the pure product (8 g) as colourless crystals which melt at 93° C.

(iv) Preparation of 1-(propan-2-on-1-yl)-4-t-butylcyclohexane Carboxaldehyde

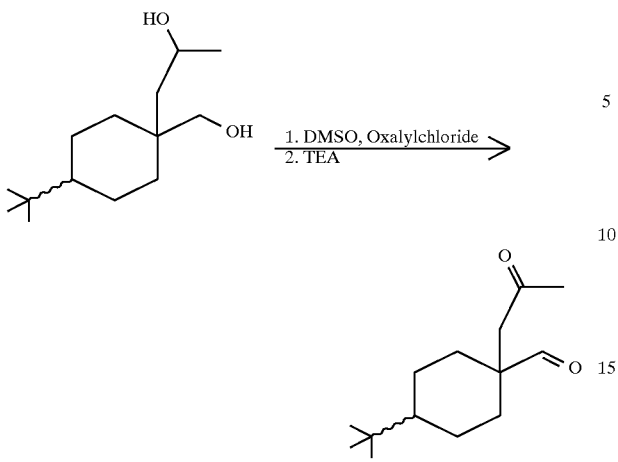

To a solution of oxalylchloride (21.0 g, 0.165 mol) in dichloromethane (50 ml) is added dimethylsulfoxide (21 ml) in dichloromethane (50 ml) at −70° C. The reaction mixture is stirred for 5 min. and 1-hydroxy-methyl-1-(2-hydroxyprop-1-yl)-4-t-butylcyclohexane (17.0 g, 0.075 mol) is added. The reaction mixture is stirred for 30 min. at −70° C. Triethylamine (100 ml) is then added and the reaction mixture is allowed to warm to room temperature. The reaction mixture is washed with water and brine. The organic layer is dried with magnesium sulfate and evaporated in vacuo to yield 15 g of a crystalline solid which melts at 68°–72° C. It is used in the next step without further purification.

(v) Preparation of 8-t-butyl-spiro[4,5]dec-3-en-2-one

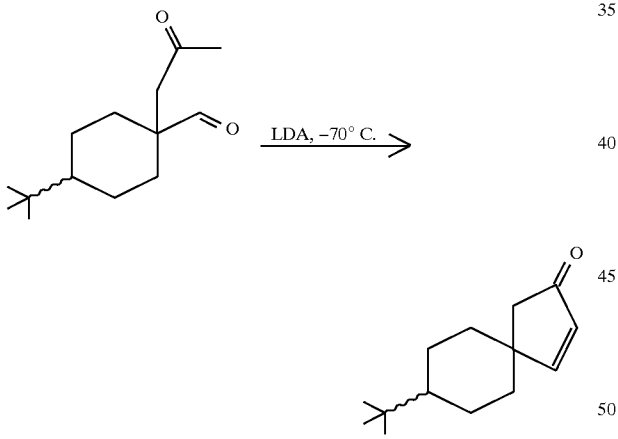

To a solution of 1-(propan-2-one-1-yl)-4-t-butylcyclohexane carboxaldehyde (14 g, 0.0625 mol) in tetrahydrofuran (200 ml) cooled to −70° C. is added a 2M solution of lithium diisopropylamide (35 ml) in tetrahydrofuran. The mixture is stirred at −70° C. for 1h and is then allowed to warm to −20° C. Aqueous saturated ammonium chloride (100 ml) is then added and the phases are separated. The organic layer is dried with magnesium sulfate and evaporated in vacuo. The crude product is dissolved in toluene (200 ml) to which p-toluenesulfonic acid (0.3 g) is added. The solution is heated to reflux for 30 min. After cooling the acid is removed by washing with 5% aqueous sodium carbonate. Drying and evaporating the solvent yields 11 g of a thick oil which is purified by flash chromatography (silica, light petroleum/ethylacetate 10:1).

(vi) Preparation of 8-t-butyl-spiro[4,5]decane-2-one

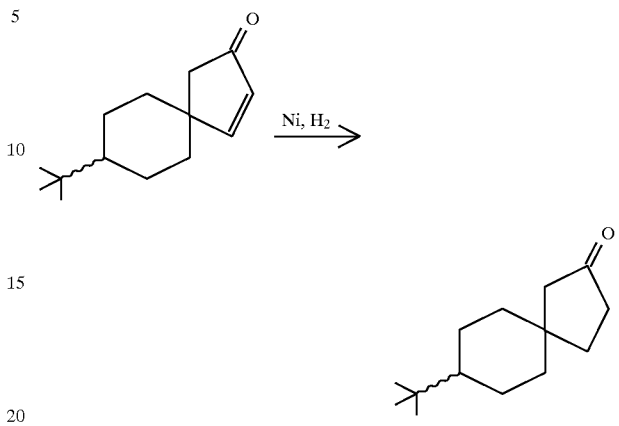

8-t-butyl-spiro[4,5]dec-3-en-2-one (7.5 g, mol) in ethanol (100 ml) is hydrogenated on a mixture of Raney Nickel and palladium on charcoal (50° C./60 psi) until hydrogen uptake ceases. The catalyst is filtered off and the solvent evaporated in vacuo. The crude product is purified by flash chromatography (silica, toluene/acetone 10:1). M.p. 78°–82° C.

(vii) Preparation of 2-Amino-spiro(4,5)decane Derivatives

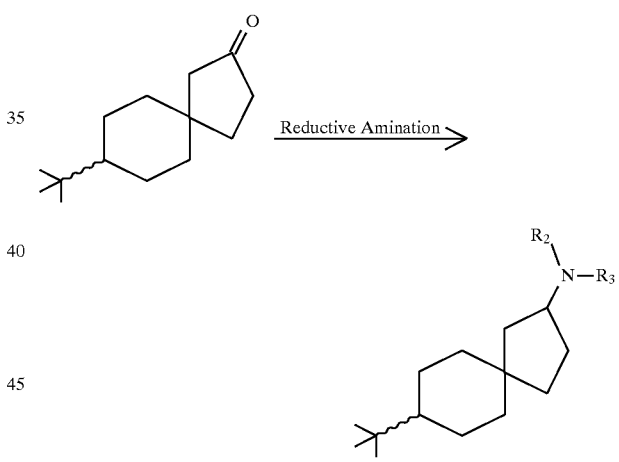

The title compounds are prepared by dissolving the (substituted) spiro(4,5)decane-2-one (4 mmol), an amine of formula $HNR_2R_3$ (4.2 mmol) and zinc chloride 0.4 g (3 mmol) in 20 ml dry methanol. Sodium cyanoborohydride (0.31 g, 5 mmol) is then added and the mixture is stirred over night at room temperature. The solvent is then distilled off in vacuo and the residue is taken up in ethylacetate (20 ml), washed with 1N sodium hydroxide (20 ml) and water (20 ml). The organic layer is dried with magnesium sulphate, filtered and evaporated in vacuo to yield the crude product which might be further purified by chromatography on silica using mixtures with varying amounts of toulene/ethylacetate/triethylamine as the eluent.

The compounds according to the invention have been prepared via the above described method as detailed below in Table Ia:

TABLE Ia

Formula I (n = 0)

| Example | R₁ | R₂ | R₃ | Acid |
|---|---|---|---|---|
| 1 | t-butyl | | —CH₂CH₂CH(CH₃)CH₂CH₂— | — |
| 2 | t-butyl | H | 3-heptyl | — |
| 3 | t-butyl | H | cyclohexyl | — |
| 4 | t-butyl | | cis-—CH₂CH(CH₃)OCH(CH₃)CH₂— | — |
| 5 | t-butyl | | —CH₂CH(CH₃)CH₂CH(CH₃)CH₂— | — |
| 6 | t-butyl | H | 3-methylcyclohexyl | — |
| 7 | t-butyl | H | 4-methylcyclohexyl | — |
| 8 | t-butyl | H | i-butyl | — |
| 9 | t-butyl | methyl | cyclohexyl | — |
| 10 | t-butyl | H | cyclopentyl | — |
| 11 | t-butyl | H | cycloheptyl | — |
| 12 | t-butyl | H | 4-chlorobenzyl | — |
| 13 | t-butyl | | —(CH₂)₂—O—(CH₂)₂— | — |
| 14 | t-butyl | n-butyl | n-butyl | — |
| 15 | t-butyl | methyl | phenyl | — |
| 16 | t-butyl | H | phenyl | — |
| 17 | t-amyl | H | cyclohexyl | — |
| 18 | t-butyl | | —CH₂CH(CH₃)(CH₂)₃— | — |
| 19 | t-amyl | | —(CH₂)₂CH(CH₃)(CH₂)₂— | — |
| 20 | t-amyl | methyl | cyclohexyl | — |
| 21 | t-butyl | | —(CH₂)₆— | — |
| 22 | t-butyl | —H | methyl | — |
| 23 | t-butyl | —H | ethyl | — |
| 24 | t-butyl | —H | n-propyl | — |
| 25 | t-butyl | —H | i-propyl | — |
| 26 | t-butyl | —H | n-butyl | — |
| 27 | t-butyl | —H | t-butyl | — |
| 28 | t-amyl | —H | methyl | — |
| 29 | t-amyl | —H | ethyl | — |
| 30 | t-amyl | —H | n-propyl | — |
| 31 | t-amyl | —H | n-butyl | — |
| 32 | t-amyl | —H | i-butyl | — |
| 33 | t-amyl | —H | t-butyl | — |
| 34 | t-amyl | —H | phenyl | — |
| 35 | t-amyl | | —(CH₂)₅— | — |
| 36 | t-amyl | | —CH₂CH(CH₃)—O—CH(CH₃)CH₂— | — |
| 37 | t-butyl | —H | —H | — |
| 38 | t-amyl | —H | —H | — |
| 39 | n-butyl | —H | phenyl | — |
| 40 | n-butyl | —H | cyclohexyl | — |
| 41 | n-butyl | —H | methyl | — |
| 42 | n-butyl | —H | ethyl | — |
| 43 | n-butyl | —H | n-propyl | — |
| 44 | n-butyl | —H | i-propyl | — |
| 45 | n-butyl | —H | n-butyl | — |
| 46 | n-butyl | —H | i-butyl | — |
| 47 | n-butyl | —H | t-butyl | — |
| 48 | n-butyl | n-butyl | phenyl | — |
| 49 | t-amyl | —H | cyclohexyl | — |
| 50 | t-amyl | methyl | phenyl | — |
| 51 | t-amyl | methyl | methyl | — |
| 52 | t-amyl | methyl | ethyl | — |
| 53 | t-amyl | methyl | n-propyl | — |
| 54 | phenyl | —H | methyl | — |
| 55 | phenyl | -butyl | phenyl | — |
| 56 | phenyl | —H | cyclohexyl | — |
| 57 | phenyl | | —CH₂CH(CH₃)CH₂CH(CH₃)CH₂— | — |
| 58 | phenyl | | —CH₂CH(CH₃)—O—CH(CH₃)CH₂— | — |
| 59 | —H | methyl | methyl | — |
| 60 | t-amyl | methyl | n-hexyl | — |
| 61 | phenyl | methyl | n-hexyl | — |
| 62 | cyclohexyl | —H | n-butyl | — |
| 63 | cyclohexyl | —H | i-propyl | — |
| 64 | cyclohexyl | —H | n-pentyl | — |
| 65 | cyclohexyl | —H | t-amyl | — |
| 66 | cyclohexyl | —H | s-butyl | — |
| 67 | t-butyl | methyl | ethyl | — |
| 68 | t-butyl | ethyl | ethyl | — |
| 69 | t-butyl | n-hexyl | n-hexyl | — |
| 70 | t-butyl | —H | n-pentyl | — |
| 71 | t-butyl | —H | allyl | — |
| 72 | t-butyl | ethyl | n-pentyl | — |
| 73 | t-butyl | n-propyl | n-pentyl | — |
| 74 | t-butyl | n-butyl | n-pentyl | — |

TABLE Ia-continued

Formula I (n = 0)

| Example | $R_1$ | $R_2$ | $R_3$ | Acid |
|---|---|---|---|---|
| 75 | t-butyl | s-butyl | n-pentyl | — |
| 76 | t-butyl | i-propyl | n-pentyl | — |
| 77 | t-butyl | cyclohexyl | n-pentyl | — |
| 78 | t-butyl | methyl | n-pentyl | — |
| 79 | t-butyl | allyl | cyclohexyl | — |
| 80 | t-butyl | methyl | cyclohexyl | — |
| 81 | t-butyl | —H | t-butyl | — |
| 82 | t-butyl | —H | cyclohexylmethyl | — |
| 83 | t-butyl | —H | 1-ethylpropyl | — |
| 84 | t-butyl | —H | 2-methylcyclohexyl | — |
| 85 | t-butyl | —H | 2-norbornyl | — |
| 86 | t-butyl | —H | 2-adamantyl | — |
| 87 | t-butyl | —H | 3-methylcyclohexyl | — |
| 88 | t-butyl | —H | 4-methylcyclohexyl | — |
| 89 | t-butyl | —H | 4-ethylcyclohexyl | — |
| 90 | t-butyl | —H | 2-ethylcyclohexyl | — |
| 91 | t-butyl | methyl | cyclohexylmethyl | — |
| 92 | t-butyl | ethyl | cyclohexylmethyl | — |
| 93 | t-butyl | propyl | cyclohexylmethyl | — |
| 94 | t-butyl | methyl | 1-ethylpropyl | — |
| 95 | t-butyl | ethyl | 1-ethylpropyl | — |
| 96 | t-butyl | n-propyl | 1-ethylpropyl | — |
| 97 | t-butyl | i-propyl | i-propyl | — |
| 98 | t-butyl | —H | cyclohexylmethyl | — |
| 99 | t-butyl | —H | 1-propylbutyl | — |
| 100 | t-butyl | —H | 2-cyclohexylethyl | — |
| 101 | t-butyl | —H | 2-heptyl | — |
| 102 | t-butyl | —H | 3-heptyl | — |
| 103 | t-butyl | allyl | allyl | — |
| 104 | t-butyl | —H | n-heptyl | — |
| 105 | t-butyl | —H | 2-octyl | — |
| 106 | t-butyl | —H | 1,1,3-trimethylbutyl | — |
| 107 | t-butyl | —H | 1,5-dimethylhexyl | — |
| 108 | t-butyl | —H | 2-cyclohex-1-enyl-ethyl | — |
| 109 | t-butyl | —H | 4-t-butyl-cyclohexyl | — |
| 110 | t-butyl | —H | 1,3-dimethylbutyl | — |
| 111 | t-butyl | —H | 2-t-butylethyl | — |
| 112 | t-butyl | —H | 1,3-dimethylpentyl | — |
| 113 | cyclohexyl-methyl | | —CH$_2$CH$_2$CH(—CH$_2$—)$_4$CHCH$_2$— | — |
| 114 | t-butyl | | —CH$_2$CH$_2$(1,2-benzylene)CH$_2$— | — |
| 115 | cyclohexyl-methyl | —H | n-octyl | — |
| 116 | t-butyl | | —CH$_2$CH$_2$CH$_2$CH(—CH$_2$—)$_4$CH— | — |
| 117 | t-butyl | methyl | 2-cyclohexylethyl | — |
| 118 | t-butyl | ethyl | 2-cyclohexylethyl | — |
| 119 | t-butyl | n-propyl | 2-cyclohexylethyl | — |
| 120 | t-butyl | —H | 4-methylcyclohexyl-methyl | — |
| 121 | t-butyl | methyl | 2-methylpropyl | — |
| 122 | t-butyl | i-propyl | 2-cyclohexylethyl | — |
| 123 | t-butyl | n-propyl | 2-methylpropyl | — |
| 124 | t-butyl | —H | C(CH$_3$)=CHCOCH$_2$CH(CH$_3$)$_2$ | — |
| 125 | t-butyl | —CH$_3$ | —CH$_2$—(1-Methyl-cyclohexyl) | — |
| 126 | t-butyl | —C$_2$H$_5$ | —CH$_2$—(1-Methyl-cyclohexyl) | — |
| 127 | t-butyl | —C$_3$H$_7$ | —CH$_2$—(1-Methyl-cyclohexyl) | — |
| 128 | t-butyl | —CH$_3$ | -2-Norbornyl | — |
| 129 | t-butyl | —C$_2$H$_5$ | -2-Norbornyl | — |
| 130 | t-butyl | —C$_3$H$_7$ | -2-Norbornyl | — |
| 131 | t-butyl | —CH$_3$ | —CH$_2$—C(CH$_3$)$_3$ | — |
| 132 | t-butyl | —C$_2$H$_5$ | —CH$_2$—C(CH$_3$)$_3$ | — |
| 133 | t-butyl | —C$_3$H$_7$ | —CH$_2$—C(CH$_3$)$_3$ | — |
| 134 | t-butyl | —H | —CH$_2$—C(CH$_3$)$_3$ | — |
| 135 | 1,1,3,3-tetramethyl- | | —(CH$_2$)$_2$CH(CH$_3$)(CH$_2$)$_2$— | — |

TABLE Ia-continued

Formula I (n = 0)

| Example | $R_1$ | $R_2$ | $R_3$ | Acid |
|---|---|---|---|---|
| 136 | 1,1,3,3-tetramethyl-butyl |  | —CH$_2$CH(CH$_3$)CH$_2$CH(CH$_3$)CH$_2$— | — |
| 137 | 1,1,3,3-tetramethyl-butyl | —H | —CH$_2$—CH(CH$_3$)$_2$ | — |
| 138 | t-butyl | —H | -2-Decalyl | HCl |
| 139 | 1-methyl-1 cyclohexyl-ethyl | —H | —CH$_2$—CH(CH$_3$)$_2$ | — |
| 140 | 1-methyl-1-cyclohexyl-ethyl | —CH$_3$ | -n-C$_6$H$_{13}$ | — |
| 141 | 1-methyl-1-cyclohexyl-ethyl |  | —(CH$_2$)$_2$CH(CH$_3$)(CH$_2$)$_2$— | — |
| 142 | 1-methyl-1-cyclohexyl-ethyl | —H | —C$_6$H$_{11}$ | — |
| 143 | t-butyl | —CH$_2$—CH(CH$_3$)$_2$ | —CH$_2$—CH(CH$_3$)$_2$ | — |
| 144 | t-butyl | —H | —(CH$_2$)$_2$OCH$_3$ | — |
| 145 | t-C$_4$H$_9$ | —H | —CH$_2$—(2-THF) | — |
| 146 | t-butyl | —H | —CH$_2$CH(OCH$_3$)$_2$ | — |
| 147 | t-butyl | —(CH$_2$)$_2$OCH$_3$ | —(CH$_2$)$_2$OCH$_3$ | — |
| 148 | t-butyl | —CH$_3$ | —CH$_2$CH(OCH$_3$)$_2$ | — |
| 149 | t-butyl | —CH$_3$ | —CH$_2$-2-(1,3-Dioxolanyl) | — |
| 150 | t-butyl | —CH$_3$ | —(CH$_2$)$_2$OCH$_3$ | — |
| 151 | t-butyl | —CH$_3$ | —CH$_2$—(2-THF) | — |
| 152 | t-butyl | —C$_2$H$_5$ | —CH$_2$—(2-THF) | — |
| 153 | t-butyl | —H | —CH$_2$CH(OC$_2$H$_5$)$_2$ | — |
| 154 | t-butyl | —C$_2$H$_5$ | —CH$_2$CH(OCH$_3$)$_2$ | — |
| 155 | t-butyl | —CH$_3$ | —CH$_2$CH(OC$_2$H$_5$)$_2$ | — |
| 156 | t-butyl | —C$_2$H$_5$ | —CH$_2$CH(OC$_2$H$_5$)$_2$ | — |
| 157 | t-butyl | —H | —CH$_2$—(1-Methyl-cyclohexyl) | HCl |
| 158 | t-butyl | —H | —CH$_2$—(1-Methyl-cyclohexyl) | HBr |
| 159 | t-butyl | —H | —CH$_2$—(1-Methyl-cyclohexyl) | H$_3$BO$_3$ |
| 160 | t-butyl | —H | —CH$_2$—(1-Methyl-cyclohexyl) | ½ HOOC—COOH |
| 161 | t-butyl | —H | —CH$_2$—(1-Methyl-cyclohexyl) | CH$_3$COOH |
| 162 | t-butyl | —H | —CH$_2$—(1-Methyl-cyclohexyl) | CF$_3$COOH |
| 163 | t-butyl | —H | —CH$_2$—(1-Methyl-cyclohexyl) | C$_3$H$_7$COOH |
| 164 | t-butyl | —H | —CH$_2$—(1-Methyl-cyclohexyl) | C$_5$H$_{11}$COOH |
| 165 | t-butyl | —H | CH$_2$—(1-Methyl-cyclohexyl) | C$_{11}$H$_{23}$COOH |
| 166 | t-butyl | —H | —CH$_2$—(1-Methyl-cyclohexyl) | C$_{15}$H$_{31}$COOH |
| 167 | t-butyl | —H | —CH$_2$—(1-Methyl-cyclohexyl) | C$_6$H$_5$B(OH)$_2$ |
| 168 | t-butyl | —H | —CH$_2$—(1-Methyl-cyclohexyl) | Saccharin |
| 169 | t-butyl | —H | —CH(C$_2$H$_5$)C$_4$H$_9$ | HCl |
| 170 | t-butyl | —H | —CH(C$_2$H$_5$)C$_4$H$_9$ | HBr |
| 171 | t-butyl | —H | —CH(C$_2$H$_5$)C$_4$H$_9$ | H$_3$BO$_3$ |
| 172 | t-butyl | —H | —CH(C$_2$H$_5$)C$_4$H$_9$ | ½ HOOC—COOH |
| 173 | t-butyl | —H | —CH(C$_2$H$_5$)C$_4$H$_9$ | CH$_3$COOH |
| 174 | t-butyl | —H | —CH(C$_2$H$_5$)C$_4$H$_9$ | CF$_3$COOH |
| 175 | t-butyl | —H | —CH(C$_2$H$_5$)C$_4$H$_9$ | C$_3$H$_7$COOH |
| 176 | t-butyl | —H | —CH(C$_2$H$_5$)C$_4$H$_9$ | C$_5$H$_{11}$COOH |
| 177 | t-butyl | —H | —CH(C$_2$H$_5$)C$_4$H$_9$ | C$_{11}$H$_{23}$COOH |
| 178 | t-butyl | —H | —CH(C$_2$H$_5$)C$_4$H$_9$ | C$_{15}$H$_{31}$COOH |
| 179 | t-butyl | —H | —CH(C$_2$H$_5$)C$_4$H$_9$ | C$_6$H$_5$B(OH)$_2$ |
| 180 | t-butyl | —H | —CH(C$_2$H$_5$)C$_4$H$_9$ | Saccharin |

EXAMPLES 181–223

The compounds of formula I, wherein n represents 1, 2 or 3, are obtained from the corresponding compounds of formula IIb, wherein n is 0, 1 or 2, respectively, using procedures analogous to example 1 (vii). The resulting compounds are given below in Tables Ib to Id:

TABLE Ib

Formula I (n = 1)

| Example | $R_1$ | $R_2$ | $R_3$ | Acid |
|---|---|---|---|---|
| 181 | t-butyl | —H | —H | — |
| 182 | t-butyl | —H | —$C_6H_{11}$ | — |
| 183 | t-butyl | —H | -n-$C_8H_{17}$ | — |
| 184 | t-butyl | —H | -n-$C_6H_{13}$ | — |
| 185 | t-butyl | —H | —$C_6H_{11}$ | HCl |
| 186 | t-butyl | —$CH_2$—$CH(CH_3)_2$ | —$CH_2$—$CH(CH_3)_2$ | — |
| 187 | t-butyl | —$CH_3$ | —$C_6H_{11}$ | — |
| 188 | t-butyl | —$C_2H_5$ | —$C_6H_{11}$ | — |

TABLE Ic

Formula I (n = 2)

| Example | $R_1$ | $R_2$ | $R_3$ | Acid |
|---|---|---|---|---|
| 189 | t-butyl | —H | —$C_6H_{11}$ | — |
| 190 | t-butyl | —H | —H | HCl |
| 191 | t-butyl | —$CH_3$ | —$CH_3$ | — |
| 192 | t-butyl | —H | (3-Methyl)-cyclohexyl | — |
| 193 | t-butyl | —H | —$CH(C_3H_7)C_3H_7$ | HCl |
| 194 | t-butyl | —H | —$CH(CH_3)C_5H_{11}$ | — |
| 195 | t-butyl | —H | —$C_7H_{13}$ | — |
| 196 | t-butyl | —$C_4H_9$ | -n-$C_4H_9$ | — |
| 197 | t-butyl | —H | —$CH(C_2H_5)C_4H_9$ | — |
| 198 | t-butyl | —H | -2-Decalyl | — |
| 199 | t-butyl | —$CH_3$ | —$C_6H_{11}$ | — |
| 200 | t-butyl | —$C_2H_5$ | —$C_6H_{11}$ | — |
| 201 | t-butyl | —$CH_3$ | —$CH(CH_3)C_5H_{11}$ | — |
| 202 | t-butyl | —$C_2H_5$ | —$CH(CH_3)C_5H_{11}$ | — |
| 203 | t-butyl | —$(CH_2)_5$— | | — |
| 204 | t-butyl | —$(CH_2)_2$—O—$(CH_2)_2$— | | — |
| 205 | t-butyl | —H | -(4-t-Butyl)-cyclohexyl | — |
| 206 | t-butyl | —H | -(4-Methyl)-cyclohexyl | — |
| 207 | t-butyl | —H | -(2-Methyl)-cyclohexyl | — |
| 208 | t-butyl | —H | —$C_5H_9$ | — |
| 209 | t-butyl | —H | —$(CH_2)$-2-THF | — |
| 210 | t-butyl | —$CH_3$ | —$CH(C_2H_5)C_4H_9$ | — |
| 211 | t-butyl | —$C_2H_5$ | —$CH(C_2H_5)C_4H_9$ | — |
| 212 | t-butyl | —$C_3H_7$ | —$CH(C_2H_5)C_4H_9$ | — |

TABLE Id

Formula I (n = 3)

| Example | $R_1$ | $R_2$ | $R_3$ | Acid |
|---|---|---|---|---|
| 213 | t-butyl | H | H | — |
| 214 | t-butyl | H | —$CH(CH_3)C_5H_{11}$ | — |
| 215 | t-butyl | H | —$CH(C_2H_5)C_4H_9$ | — |
| 216 | t-butyl | H | —$CH(C_3H_7)C_3H_7$ | — |
| 217 | t-butyl | H | —$C_6H_{11}$ | — |
| 218 | t-butyl | H | —$C_7H_{13}$ | — |
| 219 | t-butyl | —$(CH_2)_2$—O—$(CH_2)_2$— | | — |
| 220 | t-butyl | —$(CH_2)_5$— | | — |
| 221 | t-butyl | —$(CH_2)_2CH(CH_3)(CH_2)_2$— | | — |
| 222 | t-butyl | —$CH_2CH(CH_3)CH_2CH(CH_3)$— | | — |
| 223 | t-butyl | —$CH_2CH(CH_3)$—O—$CH(CH_3)CH_2$— | | — |

THF means tetrahydrofurfuryl, acid means that the compound is an ammonium salt of the denoted acid. All other alkyl groups are straight chains unless otherwise designated as branched chains. $C_6H_5$ means phenyl, $C_7H_{13}$ means cycloheptyl, $C_6H_{11}$ means cyclohexyl, $C_5H_9$ means cyclopentyl and $C_3H_5$ means cyclopropyl.

Physical data for the above compounds are set out in Tables II, III and IV.

TABLE II

Melting Point

| Example No. | Melting Point [°C.] |
|---|---|
| 1 | 128 |
| 3 | 67–69 |
| 4 | 70–72 |
| 5 | 50 |
| 12 | 53–57 |

TABLE III

Refractive Index

| Example No. | $n_D^{20}$ |
|---|---|
| 2 | 1.4782 |

TABLE IV

Molecular weight
(determined by mass spectrometry)

| Example No. | Calculated | Found |
|---|---|---|
| 6 | 305 | 305 |
| 7 | 305 | 305 |
| 8 | 265 | 265 |
| 9 | 305 | 305 |
| 10 | 277 | 277 |
| 11 | 305 | 305 |

Biological Data

Evaluation of In Vivo Fungicidal Activity of Test Compounds

Test compounds are dissolved in acetone and diluted with deionized water (95 parts water to 5 parts acetone) containing 0.05% TWEEN 20®, a polyoxyethylene sorbitan monolaurate surfactant manufactured by Atlas Chemical Industries, to give a concentration of 200 ppm.

The plants are sprayed with the test solutions, dried and inoculated with fungi later the same day. When disease symptom development is optimal, the plants are rated for disease control according to the rating scale shown below. Each test contains inoculated treated plants, inoculated untreated plants and a inoculated plants treated with reference fungicides. The data obtained are shown in Table V.

RATING SCALE

| Rating | Range % Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| t | no evaluation possible |

TARGETS

| Symbol | Disease | Pathogen |
|---|---|---|
| AS | Apple Scab | Venturia inaequalis |
| GDM | Grape Downy Mildew | Plasmopara viticola |
| PB | Pepper Botrytis | Botrytis cinerea |
| RB | Rice Blast | Pyricularia grisea f. sp. oryzae |
| SBC | Sugar Beet Cercospora | Cercospora beticola |
| TEB | Tomato Early Blight | Alternaria solani |
| WPM | Wheat Powdery Mildew | Erysiphe graminis f. sp. tritici |
| WSN | Wheat Septoria nodorum Blotch | Septoria nodorum |

TABLE V

| Example | AS | GDM | PB | RB | SBC | TEB | WPM | WSN |
|---|---|---|---|---|---|---|---|---|
| 1 | 6 | 9 | 8 | 0 | 6 | 0 | 7 | 7 |
| 2 | 8 | 8 | 9 | 0 | 4 | 0 | 8 | 0 |
| 3 | 8 | 5 | 9 | 0 | 6 | 8 | 8 | 8 |
| 4 | 0 | 0 | 9 | 0 | 7 | 0 | 9 | 7 |
| 5 | 6 | 5 | 9 | 0 | 7 | 0 | 8 | 4 |
| 6 | 5 | 4 | 7 | 4 | 7 | 3 | 7 | 6 |
| 7 | 4 | 3 | 7 | 0 | 8 | 4 | 7 | 7 |
| 8 | 8 | 0 | 6 | 0 | 6 | 0 | 5 | 4 |
| 9 | 8 | 2 | 8 | 0 | 4 | 0 | 7 | 6 |
| 10 | 8 | 5 | 6 | 0 | 6 | 2 | 6 | 7 |
| 11 | 7 | 6 | 8 | 0 | 5 | 5 | 6 | 6 |
| 12 | 7 | 0 | 7 | 0 | 0 | 0 | 5 | 0 |

Evaluation of In Vitro Fungicidal Activity of Test Compounds

Test compounds are dissolved in acetone then diluted with deionize water (9 parts water: 1 part acetone), and dispersed into cell well plates containing a suspension of ground fungal mycelium in a nutrient broth resulting in a final concentration of 25 ppm of the test compound. Assay plates are incubated for 3–7 days at 22° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference fungicide are included in each test.

Assay fungi include the following pathogens:

| SYMBOL | PATHOGEN |
|---|---|
| FUS OXC | Fusarium oxysporium f. sp. cucumerinum |
| PSDC HE | Pseudocercosporella herpotrichoides |
| PTYH UL | Pythium ultimum |
| RHIZ SO | Rhizoctonia solani |

| Example | FUS OXC | PSDC HE | PYTH UL | RHIZ SO |
|---|---|---|---|---|
| 1 | 0 | 7 | 7 | 9 |
| 2 | 0 | 9 | 9 | 7 |
| 3 | 0 | 0 | 1 | 0 |
| 4 | 0 | 0 | 0 | 0 |
| 5 | 0 | 0 | 0 | 0 |
| 6 | 0 | 7 | 7 | 9 |
| 7 | 0 | 7 | 7 | 9 |
| 8 | 0 | 7 | 7 | 9 |
| 9 | 0 | 7 | 7 | 9 |
| 10 | 0 | 9 | 9 | 9 |
| 11 | 0 | 9 | 0 | 9 |
| 12 | 0 | 9 | 0 | 9 |

I claim:

1. A compound of the formula I

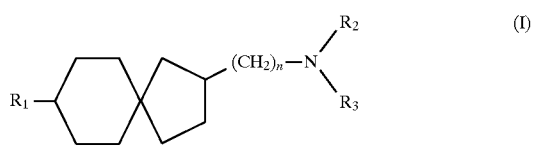

or an acid-addition salt thereof wherein $R_1$ represents an optionally substituted $C_{3-8}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group;

$R_2$ and $R_3$ together represent a saturated chain containing four or five carbon atoms optionally interrupted by oxygen atoms and which chain optionally may be aryl- or cyclopentyl fused, wherein each of the above groups is optionally substituted by one or more chlorine or fluorine atoms or $C_{1-4}$ alky, $C_{1-4}$ haloalkyl, $C_{4-6}$ cycloalkenyl or $C_{1-4}$ alkoxy groups; and n represents zero or an integer from 1 to 3.

2. The compound according to claim 1 wherein n represents 0.

3. A fungicidal composition which comprises at least two carriers, at least one of which is a surface active agent and, as active ingredient, a compound of the general formula I

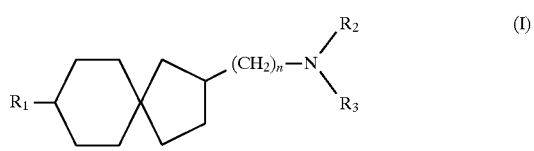

or an acid-addition salt thereof, wherein $R_1$ represents an optionally substituted $C_{3-8}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group;

$R_2$ and $R_3$ each independently represent hydrogen or an optionally substituted alkyl, alkenyl, alkynyl, cycloalkyl, cycloalkylalkyl, bicycloalkyl, tricycloalkyl, alkoxyalkyl, aralkyl, aryl or haloaralkyl, a 4- to 6-membered heterocyclyl, tetrahydrofuryl or dioxolanyl group, or $R_2$ and $R_3$, together represent an optionally substituted, saturated or unsaturated chain which may optionally contain one or more oxygen, nitrogen or sulphur atoms and which may optionally be aryl- or cycloalkyl-fused; and n represents zero or an integer from 1 to 3.

4. A method for preventing, ameliorating or combating a disease caused by fungi which comprises applying to a locus an effective amount of a compound of the general formula I

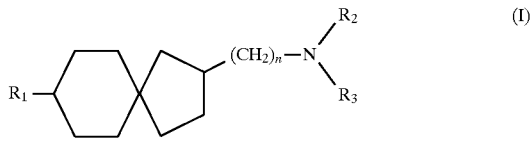

or an acid-addition salt thereof, wherein $R_1$ represents an optionally substituted $C_{3-8}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group;

$R_2$ and $R_3$ each independently represent hydrogen or an optionally substituted alkyl, alkenyl, alkynyl, cycloalkyl, cycloalkylalkyl, bicycloalkyl, tricycloalkyl, alkoxyalkyl, aralkyl, aryl or haloaralkyl, a 4- to 6-membered heterocyclyl, tetrahydrofuryl or dioxolanyl group, or $R_2$ and $R_3$, together represent an optionally substituted, saturated or unsaturated chain which may optionally contain one or more oxygen, nitrogen or sulphur atoms and which may optionally be aryl- or cyloalkyl-fused; and n represents zero or an integer from 1 to 3, or a composition as defined in claim 3.

5. The method according to claim 4, in which the locus comprises plants subject to or subjected to fungal attack, seeds of such plants or the medium in which the plants are grown or are to be grown.

6. The compound according to claim 1 selected from the group consisting of:
1-(8-tert-butyl-spiro[4.5]dec-2-yl)-4-methylpiperidine;
1-(8-tert-butyl-spiro[4.5]dec-2-yl)-2,6-dimethylmorpholine;
1-(8-tert-butyl-spiro[4.5]dec-2-yl)-3,5-dimethylpiperidine; and
1-(8-tert-butyl-spiro[4.5]dec-2-yl)-morpholine.

7. A process for the preparation of a compound of the formula I

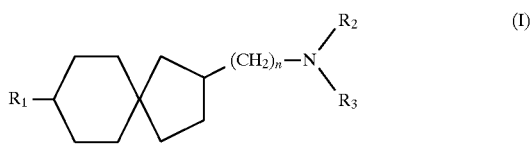

or an acid-addition salt thereof, wherein $R_1$ represents an optionally substituted $C_{3-8}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group;

$R_2$ and $R_3$ together represent a saturated chain containing four or five carbon atoms optionally interrupted by oxygen atoms and which chain optionally may be aryl- or cyclopentyl fused, wherein each of the above groups is optionally substituted by one or more chlorine or fluorine atoms or $C_{1-4}$ alkyl, $C_{1-4}$ haloallyl, $C_{4-6}$ cycloalkenyl or $C_{1-4}$ alkoxy groups; and n represents zero or an integer from 1 to 3, which comprises reaction of a compound of the formulae IIa or IIb wherein $R_1$ is as defined above and n represents 0, 1 or 2, with a compound of the general formula III

wherein $R_2$ and $R_3$ are as defined above, in the presence of a reducing agent.

8. The process according to claim 7 wherein the reducing agent is a complex metal hydride.

9. The composition according to claim 3, wherein $R_1$ represents a tertiary butyl or tertiary amyl group.

10. A fungicidal composition which comprises a carrier and, as active ingredient, a compound of the general formula I or an acid-addition salt thereof as defined in claim 1.

11. The composition according to claim 10, which comprises at least two carriers, at least one of which is a surface active agent.

12. The composition according to claim 3 wherein the compound is selected from the group consisting of
(8-tert-butyl-spiro[4.5]dec-2-yl)-(1-ethylpentyl)-amine;
(8-tert-butyl-spiro[4.5]dec-2-yl)-cyclohexyl-amine;
(8-tert-butyl-spiro[4.5]dec-2-yl)-(3-methylcyclohexyl)-amine;
(8-tert-butyl-spiro[4.5]dec-2-yl)-(4-methylcyclohexyl)-amine;
(8-tert-butyl-spiro[4.5]dec-2-yl)-isobutyl-amine;
(8-tert-butyl-spiro[4.5]dec-2-yl)-cyclohexyl-methyl-amine;
(8-tert-butyl-spiro[4.5]dec-2-yl)-cyclopentyl-amine;
(8-tert-butyl-spiro[4.5]dec-2-yl)-cycloheptyl-amine;
(8-tert-butyl-spiro[4.5]dec-2-yl)-(4-chlorobenzyl)-amine;
1-(8-tert-butyl-spiro[4.5]dec-2-yl)-4-methyl-piperidine;
1-(8-tert-butyl-spiro[4.5]dec-2-yl)-2,6-dimethyl-morpholine;
1-(8-tert-butyl-spiro[4.5]dec-2-yl)-3,5-dimethyl-piperidine; and
1-(8-tert-butyl-spiro[4.5]dec-2-yl)-morpholine.

13. The method according to claim 4 wherein $R_1$ represents a tertiary butyl or tertiary amyl group.

14. The method according to claim 4 wherein the compound is selected from the group consisting of
(8-tert-butyl-spiro[4.5]dec-2-yl)-(1-ethylpentyl)-amine;
(8-tert-butyl-spiro[4.5]dec-2-yl)-cyclohexyl-amine;
(8-tert-butyl-spiro[4.5]dec-2-yl)-(3-methylcyclohexyl)-amine;
(8-tert-butyl-spiro[4.5]dec-2-yl)-(4-methylcyclohexyl)-amine;
(8-tert-butyl-spiro[4.5]dec-2-yl)-isobutyl-amine;
(8-tert-butyl-spiro[4.5]dec-2-yl)-cyclohexyl-methyl-amine;
(8-tert-butyl-spiro[4.5]dec-2-yl)-cyclopentyl-amine;
(8-tert-butyl-spiro[4.5]dec-2-yl)-cycloheptyl-amine;
(8-tert-butyl-spiro[4.5]dec-2-yl)-(4-chlorobenzyl)-amine;
1-(8-tert-butyl-spiro[4.5]dec-2-yl)-4-methyl-piperidine;
1-(8-tert-butyl-spiro[4.5]dec-2-yl)-2,6-dimethyl-morpholine;

1-(8-tert-butyl-spiro[4.5]dec-2-yl)-3,5-dimethyl-piperidine; and 1-(8-tert-butyl-spiro[4.5]dec-2-yl)-morpholine.

15. The composition according to claim 10 wherein $R_1$ represents a tertiary butyl or tertiary amyl group.

16. The composition according to claim 10 wherein the compound is selected from the group consisting of 1-(8-tert-butyl-spiro[4.5]dec-2-yl)-4-methyl-piperidine;

1-(8-tert-butyl-spiro[4.5]dec-2-yl)-2,6-dimethyl-morpholine;

1-(8-tert-butyl-spiro[4.5]dec-2-yl)-3,5-dimethyl-piperidine; and 1-(8-tert-butyl-spiro[4.5]dec-2-yl)-morpholine.

\* \* \* \* \*